United States Patent
Zhang et al.

(10) Patent No.: US 12,304,936 B2
(45) Date of Patent: May 20, 2025

(54) INTERLEUKIN 21 PROTEIN (IL21) MUTANT AND ENCODING NUCLEIC ACID

(71) Applicant: Hyquo Molecule (Beijing) Technology Co., Ltd, Beijing (CN)

(72) Inventors: Xin Zhang, Beijing (CN); Yun Zhao, Beijing (CN); Hai Ying Hang, Beijing (CN)

(73) Assignee: Hyquo Molecule (Beijing) Technology Co., Ltd., Beijing (CN)

( * ) Notice: Subject to any disclaimer, the term of this patent is extended or adjusted under 35 U.S.C. 154(b) by 1008 days.

(21) Appl. No.: 17/296,036

(22) PCT Filed: Nov. 18, 2019

(86) PCT No.: PCT/CN2019/119088
§ 371 (c)(1),
(2) Date: May 21, 2021

(87) PCT Pub. No.: WO2020/103777
PCT Pub. Date: May 28, 2020

(65) Prior Publication Data
US 2022/0025006 A1    Jan. 27, 2022

(30) Foreign Application Priority Data
Nov. 22, 2018    (CN) .......................... 201811400000.5

(51) Int. Cl.
*A61K 38/20*    (2006.01)
*C07K 14/54*    (2006.01)
*A61K 38/00*    (2006.01)

(52) U.S. Cl.
CPC .......... *C07K 14/5406* (2013.01); *A61K 38/00* (2013.01)

(58) Field of Classification Search
CPC ..... A61K 38/20; C07K 2319/00; C07K 14/54
See application file for complete search history.

(56) References Cited

U.S. PATENT DOCUMENTS 8,475,784 B2    7/2013    Hjorth et al.

FOREIGN PATENT DOCUMENTS

| CN | 1869230 A | 11/2006 |
|---|---|---|
| CN | 101180315 A | 5/2008 |
| CN | 101553501 A | 10/2009 |
| CN | 108686202 A | 10/2018 |
| JP | 2008538290 A | 10/2008 |
| JP | 2010507382 A | 3/2010 |
| JP | 2012514586 A | 6/2012 |
| WO | 2003/087320 A2 | 10/2003 |
| WO | 2006/111524 A2 | 10/2006 |
| WO | 2008049920 A2 | 5/2008 |
| WO | 2010076339 A1 | 7/2010 |
| WO | 2010/103038 A1 | 9/2010 |

OTHER PUBLICATIONS

Bondensgaard et al. (2007) "The Existence of Multiple Conformers of Interleukin-21 Directs Engineering of a Superpotent Analogue," The Journal of Biological Chemistry vol. 282, No. 32: 23326-23336.
Bondensgaard et al. (2007) "The Existence of Multiple Conformers of Interleukin-21 Directs Engineering of a Superpotent Analogue," The Journal of Biological Chemistry vol. 282, No. 02: 23326-23336.
Zhang et al. (2014) "Building highly active cytokine interleukin IL-21 based on the molecular conformation design," Thesis, College of Chemistry Central China Normal University, 58 pages English abstract considered.
Zhou et al. (2014) "In Silico study of the increase in potency about cytokine interleukin-21," Thesis, College of Chemistry Central China Normal University, 55 pages English abstract considered.
Search Report dated Feb. 26, 2020, corresponding to International Application No. PCT/CN2019/119088 (filed Nov. 18, 2019), 4 pp.
Office Action and Search Report dated Nov. 26, 2021, corresponding to Chinese Patent Application No. CN201811400000.5, 8 pages.

*Primary Examiner* — Dong Jiang

(74) *Attorney, Agent, or Firm* — LEYDIG, VOIT & MAYER, LTD.

(57) ABSTRACT

The invention relates to an interleukin-21 protein (IL21) mutant and application thereof. The mutant is with ILE at position 16 and SER at position 70 of the amino acid sequence of the wild-type IL21 both mutating into CYS, and a disulfide bond forming between the two mutated CYSs. The amino acid sequence of the wild-type IL21 is shown in SEQ ID NO. 1. The invention also relates to a fusion protein containing the IL21 mutant protein and a use of the IL21 mutant protein or the fusion protein in the preparation of a medicine and, preferably, the medicine regulates or activates immunity or are an anti-tumor medicine. The invention also relates to the use of the IL21 mutant, the IL21/4 mutant or the fusion protein in the preparation of a formulation for promoting the differentiation and proliferation of B cell, the differentiation and proliferation of T cell, the differentiation and proliferation of NK cell.

6 Claims, 8 Drawing Sheets
Specification includes a Sequence Listing.

INTERLEUKIN 21 PROTEIN (IL21) MUTANT AND ENCODING NUCLEIC ACID

CROSS-REFERENCE TO RELATED APPLICATIONS

This application is a U.S. National Stage Application filed under 35 U.S.C. § 371 of International Application No. PCT/CN2019/119088, filed Nov. 18, 2019, which claims the benefit of Chinese Application No. 201811400000.5, filed Nov. 22, 2018. Both of these applications are hereby incorporated by reference in their entireties.

FIELD OF THE INVENTION

The present invention belongs to the field of medical technology, and in particular, relates to an interleukin 21 protein (IL21) mutant and application thereof.

BACKGROUND OF THE INVENTION

In order to solve the problem of immunosuppression in tumor immunotherapy, the treatment with a cytokine and small molecule inhibitor may play a role in immune regulation. The treatment with a cytokine and small molecule inhibitor may specifically suppress inhibitory cell subsets, of their number or function, or activate an anti-tumor effector cell by immunostimulatory molecules to enhance the anti-tumor immune response of a patient. IL2 (Interleukin-2) is not only an important mediator in immune response, but also known as one of the most powerful anti-tumor cytokines, which has a wide range of biological activities. IL2 may directly act on a thymic T cell, promote the differentiation of Treg cell, suppress autoimmunity, and can also promote the differentiation of an initial T cell into effector T cell and memory T cell, which can be activated by antigen stimulation. This can protect a human against being infection. However, systemic administration of IL2 may lead to a strong adverse reaction, which limits the therapeutic dose of IL2[1-2]. In addition, the plasma half-life of IL2 is short (about 0.5-2 hours)[3], so that the optimal dose in local microenvironment of tumor cannot be achieved. This also limits its clinical application.

In the family of cytokines, IL2, IL15 and IL21 all belong to a common cytokine receptor γ chain family. They can all promote the activity of T cell and NK cell and enhance their lethal effect on target cell. These features make them be an attractive cytokine in tumor immunotherapy study[4-5].

IL21 (Interleukin-21), a type I cytokine found in 2000, belongs to the γc family, which consists of 134 amino acids. It is mainly secreted by CD4+T cell subset, such as TH17 cell and TFH (T follicular helper) cell. NKT cell can also secrete a high level of IL21[19-20]. It has been reported that IL21 receptor (IL21R) is expressed on the surface of T cell, B cell, NK cell, dendritic cell and monocyte/macrophage, and IL21 is a cytokine with a wide range of immunomodulatory effects.

Many preclinical tests suggested that IL21 resists tumor by various mechanisms, including the innate immune system and the acquired immune system[6]. IL21 has been approved to enter a human clinical trial to treat melanoma and renal cancer, demonstrating a good therapeutic effect[7-8]; IL21 can enhance the response of NK cell to pancreatic cancer cell pre-coated with cetuximab[9]; A fusion protein constructed by IL21 and monoclonal antibody Rituximab (anti-CD20) was shown to directly induce apoptosis or kill non-Hodgkin's lymphoma (NHL) through effector cell in an animal experiment[10].

Our previous studies have found that IL21 can significantly improve the tumor-killing effect of the antibody (Herceptin) of breast cancer by transforming M2 macrophage (which increases the drug resistance and malignancy of tumor) into M1 macrophage (which has anti-tumor function) in a mouse breast cancer model[11].

Meanwhile, many clinical application studies on IL21 suggested that the toxic side effects of IL21 are less than those of IL2 or IFN-α at same dose, which are mainly manifested as a mild symptom, such as fever, fatigue, headache, rash etc., and also manifested as a serious symptom, such as abdominal pain, thrombocytopenia, hypophosphatemia, liver function damage, etc. Nevertheless, at a usual dose of 30 g/kg, the incidence of various toxic side effects is still up to 100%[12]. This problem is necessarily to be handled carefully in systemic administration. In fact, although the clinical application of IL21 has been studied for many years, the trials are still in the preclinical phase I and phase II. An important reason is that there is a problem of high incidence of toxic side effects.

In order to increase the effective concentration of cytokine in local area around tumor to avoid systemic toxic reaction, some researchers try to deliver cytokine taking advantage of the targeting ability of an antibody. The combination of the immunotherapeutic ability of cytokine and the targeted anti-tumor reaction of antibody may result high concentration of cytokines in local area around tumor, so as to effectively stimulate a cellular immune response. The combination of a cytokine and a cell-specific antibody are named as an immunocytokine[13].

However, some clinical studies showed that IL21 has a short plasma half-life, which is only about 3.09 hours[12]. Even though the fusion protein constructed by IL21 and monoclonal antibody has a molecular weight of up to about 180 kD, it still has a short plasma half-life. The fusion protein constructed by IL21 and Rituximab (anti-CD20) has a plasma half-life of only about 18.94 hours in an animal experiment[10], and still has a low druggability. Therefore, it is required to improve the stability of IL21 to increase its half-life and improve its druggability.

Structural analysis showed that IL21 protein has two conformations, a stable conformation and an unstable conformation, and this is a reason why IL21 has a short half-life. It has been reported that a chimeric IL21/4 may be constructed by substituting the unstable region in the protein structure of IL21 with the homologous region of IL4 (interleukin-4). The results showed that the chimeric IL21/4 has a unique and stable protein conformation, and has an improved biological activity[14].

In our previous studies, we have established a stable mammalian cell surface protein display system for in vitro control of protein conformation (see CN201410803422, CN201810795499), which can be used to screen and identify a rationally designed protein or random mutation. In the present invention, we will use this system to stably display interleukin-21 (IL21), and optimize and obtain a group of mutant IL21 proteins through the design based on protein structure analysis.

REFERENCES

1. Roth J A, Cristiano R J, Gene therapy for cancer: what have we done and where are we going? J. Natl. Cancer Inst. 1997; 89:21-39.

2. Zatloukal K, Schneeberger A, Berger M et al. Elicitation of a systemic and protective anti-melanoma immune response by an IL-2 based vaccine. Assessment of critical cellular and molecular parameters. J. Immunol. 1995; 154:3406-3419.
3. Lotze M T, et al. In vivo administration of purified human interleukin 2.I. Half-life and immunologic effects of the Jurkat cell line-derived interleukin 2. [J] Immunol. 1985; 134(1):157-66.
4. Overwijk, W W., Schluns, K. S. Functions of γc cytokines in immune homeostasis: Current and potential clinical applications[J]. Clin Immunol. 2009; 132(2):153-165.
5. Malek T R, Castro I. Interleukin-2 Receptor Signaling: At the Interface between Tolerance and Immunity[J]. Immunity. 2010; 33(2):153-165.
6. Rosanne S, Warren J. L. Interleukin-21: Basic Biology and Implications for Cancer and Autoimmunity[J]. Annu. Rev. Immunol. 2008.26:57-79.
7. Schmidt H, Brown J, Mouritzen U, et al. Safety and clinical effect of subcutaneous human Interleukin-21 in patients with metastatic melanoma or renal cell carcinoma: a phase I trial[J]. Clin Cancer Res. 2010; 16 (21):5312-9.8.
8. Davis I D, Skrumsager B K, Cebon J, et al. An open-label, two-arm, phase I trial of recombinant human interleukin-21 in patients with metastatic melanoma [J]. Clin Cancer Res. 2007; 13 (12):3630-6.
9. McMichael E L, Jaime-Ramirez A C, Guenterberg K D, et al. IL21 Enhances Natural Killer Cell Response to Cetuximab-Coated Pancreatic Tumor Cells [J]. Clin Cancer Res. 2017; 23 (2):489-502.
10. Bhatt S, Parvin S, Zhang Y, et al. Anti-CD20-interleukin-21 fusokine targets malignant B cells via direct apoptosis and NK-cell-dependent cytotoxicity [J]. Blood. 2017; 129(16):2246-2256.
11. Xu M, Liu M, Du X, et al. Intratumoral Delivery of IL-21 Overcomes Anti-Her2/Neu Resistance through Shifting Tumor-Associated Macrophages from M2 to M1 Phenotype [J]. J Immunol. 2015; 194 (10):4997-5006.
12. Thompson J A, Curti B D, Redman B G, et al. Phase I Study of Recombinant Interleukin-21 in Patients With Metastatic Melanoma and Renal Cell Carcinoma [J]. Clin Oncol, 2008 Apr. 20; 26(12):2034-9.
13. Recombinant Antibody, SHEN Beifen, CHEN Zhinan, LIU Minpei, Science Press, 2005, P 373.
14. Kent B, Jens B, Dennis M, et al. The Existence of Multiple Conformers of Interleukin-21 Directs Engineering of a Superpotent Analogue[J]. THE JOURNAL OF BIOLOGICAL CHEMISTRY, 2007, 282(32):23326-23336.

SUMMARY OF THE INVENTION

The invention firstly relates to an interleukin-21 protein (IL21) mutant, which is: with ILE at position 16 and SER at position 70 of the amino acid sequence of the wild-type IL21 both mutating into CYS, and a disulfide bond forming between the two mutated CYSs, wherein the amino acid sequence of the wild-type IL21 is shown in SEQ ID NO. 1.

The invention also relates to another interleukin-21 protein (IL21) mutant, which is: with ILE at position 16, VAL at position 17, SER at position 70 and LYS at position 112 of the amino acid sequence of the wild-type IL21 all mutating into CYS, and two groups of disulfide bonds forming at 16-70 and 17-112, wherein the amino acid sequence of the wild-type IL21 is shown in SEQ ID NO. 1.

The invention also relates to a mutant of interleukin-21 and interleukin-4 chimeric protein (IL21/4), which is: with ILE at position 16 and SER at position 70 of the amino acid sequences of the interleukin-21 and interleukin-4 chimera (IL21/4) both mutating into CYS, and a disulfide bond forming between the two mutated CYSs, wherein the amino acid sequence of the interleukin-21 and interleukin-4 chimeric protein (IL21/4) is shown in SEQ ID NO. 2.

The invention also relates to another mutant of interleukin-21 and interleukin-4 chimeric protein (IL21/4), which is: with ILE at position 16, VAL at position 17, SER at position 70 and LYS at position 106 of the amino acid sequence of the interleukin-21 and interleukin-4 chimera (IL21/4) all mutating into CYS, and two groups of disulfide bonds forming at 16-70 and 17-106, wherein the amino acid sequence of the interleukin-21 and interleukin-4 chimeric protein (IL21/4) is shown in SEQ ID NO. 2.

The invention also relates to a nucleotide sequence encoding the IL21 mutant or the IL21/4 mutant.

The invention also relates to a fusion protein comprising the IL21 mutant or the IL21/4 mutant, wherein the fusion protein comprises:
  (1) Functional fragment 1: IL21 mutant or IL21/4 mutant;
  (2) Functional fragment 2: having monoclonal antibody function;
    and a connecting domain that connects the different functional fragments.

The invention also relates to a use of the IL21 mutant or the IL21/4 mutant in the preparation of a medicine, which is a medicine for regulating or activating immunity or is an anti-tumor medicine.

The invention also relates to a use of the fusion protein comprising the IL21 mutant or the IL21/4 mutant in the preparation of a medicine, which is a medicine for regulating or activating immunity or is an anti-tumor medicine.

The invention also relates to a use of the IL21 mutant or the IL21/4 mutant in the preparation of a formulation for promoting the differentiation and proliferation of B cell, the differentiation and proliferation of T cell, the differentiation and proliferation of NK cell. The invention also relates to a use of the fusion protein comprising the IL21 mutant or the IL21/4 mutant in the preparation of a formulation for promoting the differentiation and proliferation of B cell, the differentiation and proliferation of T cell, the differentiation and proliferation of NK cell.

The invention also relates to a medicine or pharmaceutical composition with the IL21 mutant or the IL21/4 mutant as an active ingredient, which comprises a therapeutically effective amount of the IL21 mutant or the IL21/4 mutant and a necessary pharmaceutical excipient.

The invention also relates to a medicine or pharmaceutical composition with the fusion protein comprising the IL21 mutant or the IL21/4 mutant as an active ingredient, which comprises a therapeutically effective amount of the fusion protein and a necessary pharmaceutical excipient.

BRIEF DESCRIPTION OF THE DRAWINGS

FIG. 11 shows the proliferation of KOB cell stimulated by IL21, 16cIL21 and 16cIL21/4 proteins.

FIG. 12 shows the proliferation of CD8+T cells stimulated in vivo by fusion protein 16cIL21/4-Herceptin and Herceptin in mouse.

FIG. 13 shows the anti-tumor test results of the fusion protein 16cIL21/4-herceptin in vitro. In the figure, Control represents the control group injected with PBS; Herceptin represents the experimental group injected with Herceptin alone; IL-21$_{mutant}$–Herceptin represents the experimental group with fusion protein of 16cIL21/4 and Herceptin; and IL-21$_{mutant}$+Herceptin represents the experimental group with mixed solution of 16cIL21/4 and Herceptin, instead of a fusion protein.

DETAILED DESCRIPTION OF THE EMBODIMENTS

Figure 1:
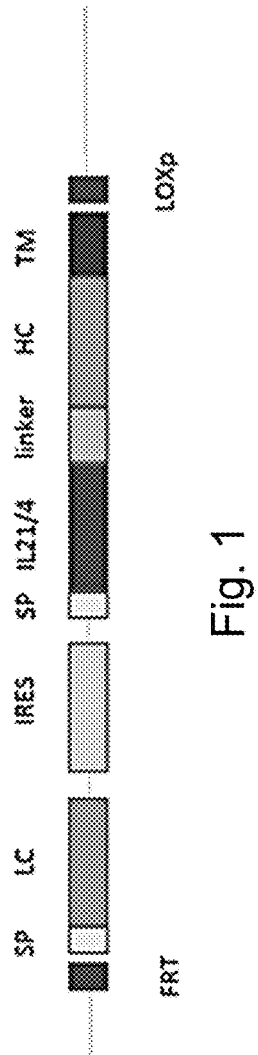
FIG. 1 shows the recombinant substitution plasmid fragment of a fusion protein of IL21/4 and Herceptin antibody.

Extraction, Purification and Preparation of Product of PCR and DNA Digestion, and Plasmid.

The product of PCR and DNA digestion was extracted by AxyPrep DNA gel extraction kit (AXYGEN). A small amount of plasmid was extracted and purified by Transgen Plasmid Mini Kit (Transgen, China). A medium amount of plasmid was extracted and purified by QIAGEN Plasmid Midi Kit. A large amount of plasmid was extracted and purified by Tiangen EndoFree Maxi Plasmid Kit. The particular procedure was carried out according to instructions.
Cell Culture.

CHO/dhFr− (Dihydrofolate reductase-deficient Chinese hamster ovary cells): The cells were cultured with IMDM medium containing 10% calf serum (Hyclone), 100 U/mL double antibody, 0.1 mM hypoxanthine and 0.016 mM thymine at 37° C. in a 5% $CO_2$ incubator.

293F cells: Human embryonic kidney cells, which were cultured with FreeStyle™ 293 Expression Medium in shake flasks at 125 rpm and 37° C. in a 5% $CO_2$ incubator.

KOB cells: Adult T lymphoma cells with high expression of IL21 receptor, which were donated by WANG Shengdian group of the Institute of Biophysics of the Chinese Academy of Sciences. The cells were cultured with RPMI1640 medium containing 10% calf serum (Hyclone) and 100 U/mL double antibody at 37° C. in a 5% $CO_2$ incubator.
Cell Transfection.
Transfection of CHO Cell.

Cell preparation: The cells were seeded in a six-well plate with the amount of 200,000 cells per well one day before transfection, so that, at the time of transfection, they reached 80% confluence, distributed evenly and grew well.

Preparation of transfection complex: 5 μl Lipo2000 and 150 ml Opti-MEM serum-free medium were mixed evenly; 2 μg target plasmid was mixed with 150 μl Opti-MEM serum-free medium evenly. After standing at room temperature for 5 minutes, these two mixtures were mixed to prepare the transfection complex, which were gently mixed and placed at room temperature for 25 minutes.

The original culture medium was removed from the six-well plate, and wells were washed with Opti-MEM serum-free medium for three times, then the transfection complex was dripped onto the cell surface, and then 500 μL of Opti-MEM serum-free medium was added. After 4-6 hours, the medium was changed into the common culture medium to continue the culture.
Transfection of 293F Cell (50 ml Culture Medium as an Example):

Cell preparation: $6 \times 10^5$-$7 \times 10^5$ cells/ml was seeded one day before transfection, and the cell density should be $1 \times 10^6$ cells/ml at the time of transfection.

Preparation of transfection complex: 50 μg of target plasmid was diluted with 2 ml OptiPROTMSFM (Invitrogen) serum-free medium and fully mixed to prepare a DNA diluent. 250 μL transfection reagent PEI was added to the DNA diluent to prepare a transfection complex, which was fully mixed and placed at room temperature for 15 minutes. The transfection complex was added into 293F cell culture medium, and then cultured in shake flasks at 125 rpm and 37° C. in a 5% $CO_2$ incubator for 96 hours.

Expression and Purification of Protein.

(1) Expression and Purification of Eukaryotic Cells.

After 293F cells being transfected by the plasmid containing the target gene, the cells were continuously cultured in a shaker for 96 hours and then centrifuged at 200 g for 3 minutes to remove cell precipitates. The supernatant medium was collected, centrifuged at 10000 g for 15 minutes to remove impurities in the culture medium, filtered with a 0.45 μm filter membrane, centrifuged in a 30 kd concentration tube at 4° C. under 3800 rmp, to concentrate 20 times of the volume.

(2) Purification of His Tag Protein.

A Sepharose high performance (Amersham Bioscience) chromatographic column filled with nickel sulfate ($NiSO_4$) was used. Buffers containing 5 mM, 30 mM, 60 mM, 90 mM, 120 mM and 250 mM imidazole were prepared respectively. Other components in the buffer were 20 mM Tris-HCL, 500 mM NaCl and 10% glycerol.

Washing and balancing the nickel column: the nickel column was firstly washed with 50 ml $ddH_2O$, and then washed and balanced with 50 ml buffer containing 5 mM imidazole. Sample loading: The supernatant containing the target protein was dripped into the nickel column, which might be repeated 2-3 times.

Elution: After loading the sample, the column was eluted with 30 ml buffer containing 5 mM, 30 mM, 60 mM, 90 mM, 120 mM and 250 mM imidazole respectively, and the eluents were collected. Ultrafiltration tubes of different specifications were selected according to the molecular weights of the target proteins. The eluents were concentrated with the ultrafiltration tubes by 50-100 times of the volumes.

Protein preservation: The finally obtained protein was packaged separately, quick-frozen in liquid nitrogen, and preserved at −80° C.

(3) Purification of Full-Length Antibody and Full-Length Antibody Fusion Protein.

A Protein A Sefinose™-5 ml (Pre-Packed Gravity Column) chromatographic column was used.

Pre-Preparation:

binding buffer: 0.1 M $Na_3PO_4$, 0.15 M NaCl, pH7.2;
elution buffer: 0.1 M citric acid, pH2.7;
neutralizing buffer: 1 M Tris-HCl, pH9.0;

Washing and balancing: the chromatographic column was firstly washed with 50 ml $ddH_2O$, then washed with 50 ml elution buffer, and then balanced with 50 ml binding buffer.

Sample loading: The supernatant containing a target protein was dripped into the chromatographic column, which might be repeated 2-3 times.

Elution: After loading the sample, the column was washed with 50 ml binding buffer to remove non-specific binding. Ten 15 ml centrifuge tubes were prepared, each being added into 800 μl pre-prepared neutralizing buffer. The protein was eluted with 30 ml elution buffer, and collected by 15 ml centrifugal tubes with neutralizing buffer, each collecting 3 ml of the elution.

Fraction collection: After the eluent being collected, the concentration of protein in each tube was detected by nanodrop. The eluent with a concentration of protein below 0.05 mg/ml was discarded. Ultrafiltration tubes of different specifications were selected according to the molecular weight of target protein. The eluent was concentrated by an ultrafiltration tube.

Protein preservation: The finally obtained protein was packaged separately, quick-frozen in liquid nitrogen, and preserved at −80° C.

Washing and preservation of chromatographic column: The chromatographic column was washed with 50 ml binding buffer, then washed with 50 ml of $ddH_2O$, and finally washed with 50 ml 20% ethanol and sealed.

Determination of Melting Temperature (Tm) of Protein.

Determination principle of melting temperature (Tm) of protein: When the temperature of protein rose with the ambient temperature and reached the melting temperature (Tm), the conformation of the protein would be destroyed. The hydrophobic core would be opened. The dye could combine with the hydrophobic region to emit a fluorescence that could be detected.

The protein to be determined was firstly adjusted to a concentration of 20-40 μM and a volume of 24 μl.

The Sypro® orange protein (5000×) was used as a dye, which was diluted to 25× with DMSO.

Preparation of 25 μl detection system: Each well of the 96-well plate was added with 24 μl protein (20-40 μM), and then with 1 μl Sypro@orang protein (25×), mixed thoroughly, and kept at room temperature away from light.

Stepone software 2.1 in qPCR instrument was used for detection, and operating and parameter setting were according to instructions.

The experimental results were determined and saved. The results were analyzed by the program of Protein Thermal Shift 3.1.

Example 1. Establishment of a CHO Cell Line that can Stably Express Chimeric IL21/4

IL21 has two protein conformations: a stable conformation and an unstable conformation. A chimeric IL21/4 was constructed by substituting the unstable region in the protein structure of IL21 with the homologous region of IL4. The results showed that the protein conformation of chimeric IL21/4 was unique and stable, with an improved biological activity. Considering that the construction of fusion protein of IL21 mutant and Herceptin was an important purpose of the experiment, after displaying the fusion protein of chimeric IL21/4 and Herceptin on the surface of a CHO working cell, it was also beneficial to detect the display efficiency of chimeric IL21/4 through detecting the constant region of Herceptin heavy chain. Therefore, we firstly displayed the fusion protein of chimeric IL21/4 and Herceptin on the surface of a CHO working cell.

In order to obtain an efficient and stable CHO cell line for displaying chimeric IL21/4, we constructed it using a protein display system established earlier in our laboratory by recombinase-mediated cassette exchange (RMCE) (see CN 201410803422 for details). A recombinant substitution plasmid fragment (FRT-IL21/4-Herceptin plasmid) was firstly constructed for displaying the fusion protein of IL21/4 and Herceptin. The fragments of the fusion protein were as follows: Herceptin light chain with a signal peptide, IRES (internal ribosome entry site), the signal peptide of the Herceptin heavy chain, IL21/4 linked to the N-terminal of the Herceptin heavy chain via a 3(G4S) linker, and the transmembrane region (TM) linked to the C-terminal of the Herceptin heavy chain. By this, the fusion protein of IL21/4 and Herceptin could be anchored and displayed on the surface of a CHO working cell by the transmembrane region. The sequence structure of the fusion protein was shown in FIG. 1 (from left to right, the fusion protein comprising: FRT recombination site, the signal peptide of the Herceptin light chain, Herceptin light chain, IRES (internal ribosome entry site) that could bind to ribosome to initiate translation, the signal peptide of the Herceptin heavy chain, IL21/4, 3(G4S) linker, Herceptin heavy chain, the transmembrane region (TM) that allowed protein molecule anchored and displayed on a cell surface, and LOXp recombination site.

Figure 2:
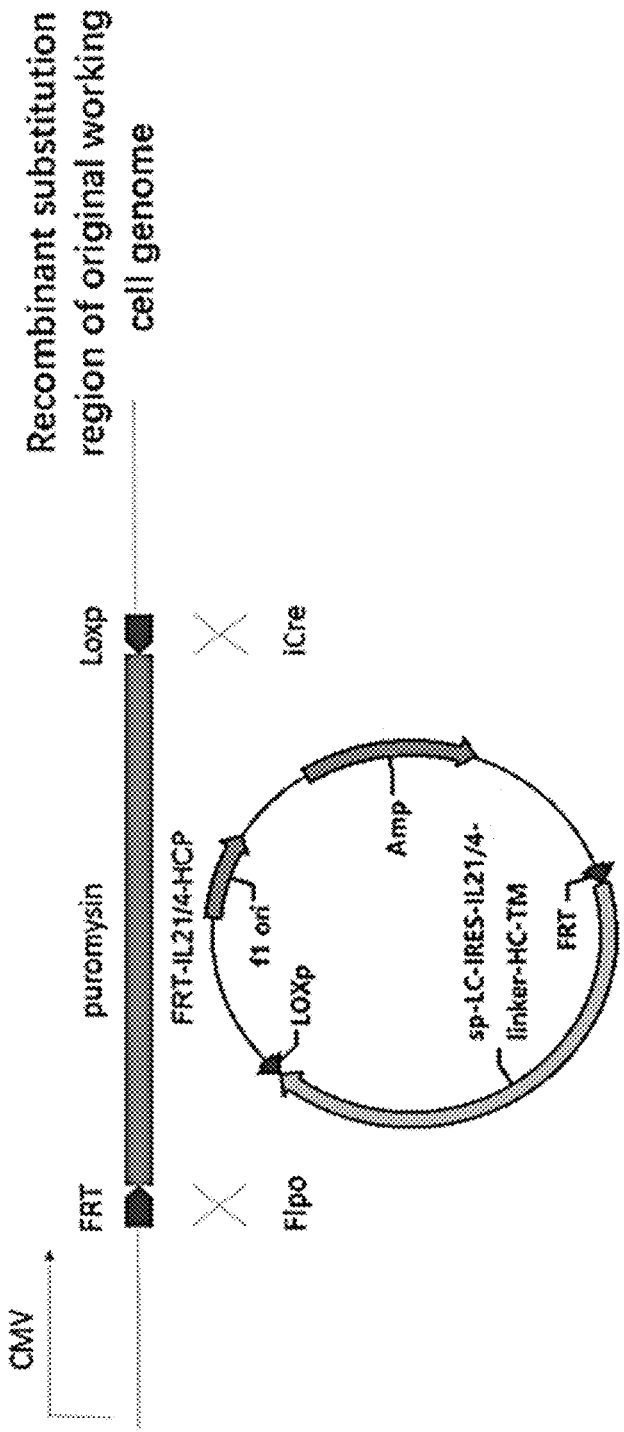
FIG. 2 is a schematic diagram showing that FRT-IL21/4-Herceptin plasmid was substituted into CHO working cell genome by homologous recombination.
Figure 2:
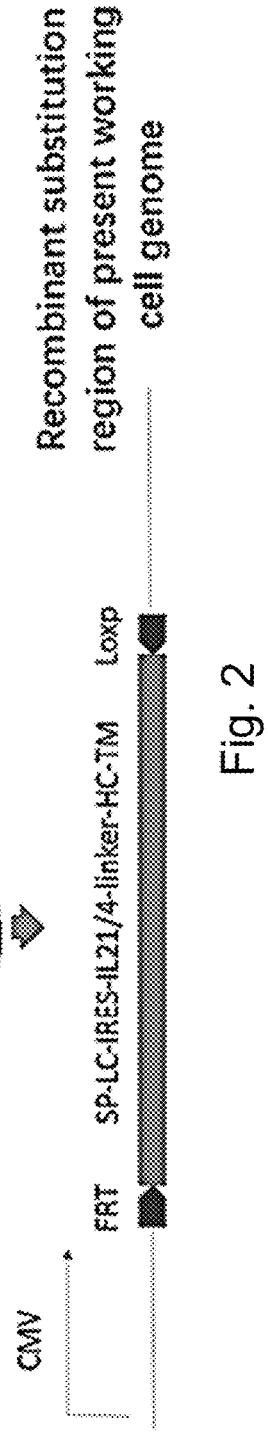

A CHO working cell established in our laboratory (see CN 201410803422 for details), whose genome was inserted with a single copy of recombinant substitution region FRT-puromysin-Loxp, were co-transfected with the FRT-IL21/4-Herceptin plasmid and the pCI-2A plasmid previously constructed in our laboratory. The fusion protein sequence of Herceptin and IL21/4 between Loxp and FRT sites in FRT-IL21/4-Herceptin plasmid could be recombined and substituted into the genome of the CHO working cell in single-copy, as shown in FIG. 2.

Figure 3:
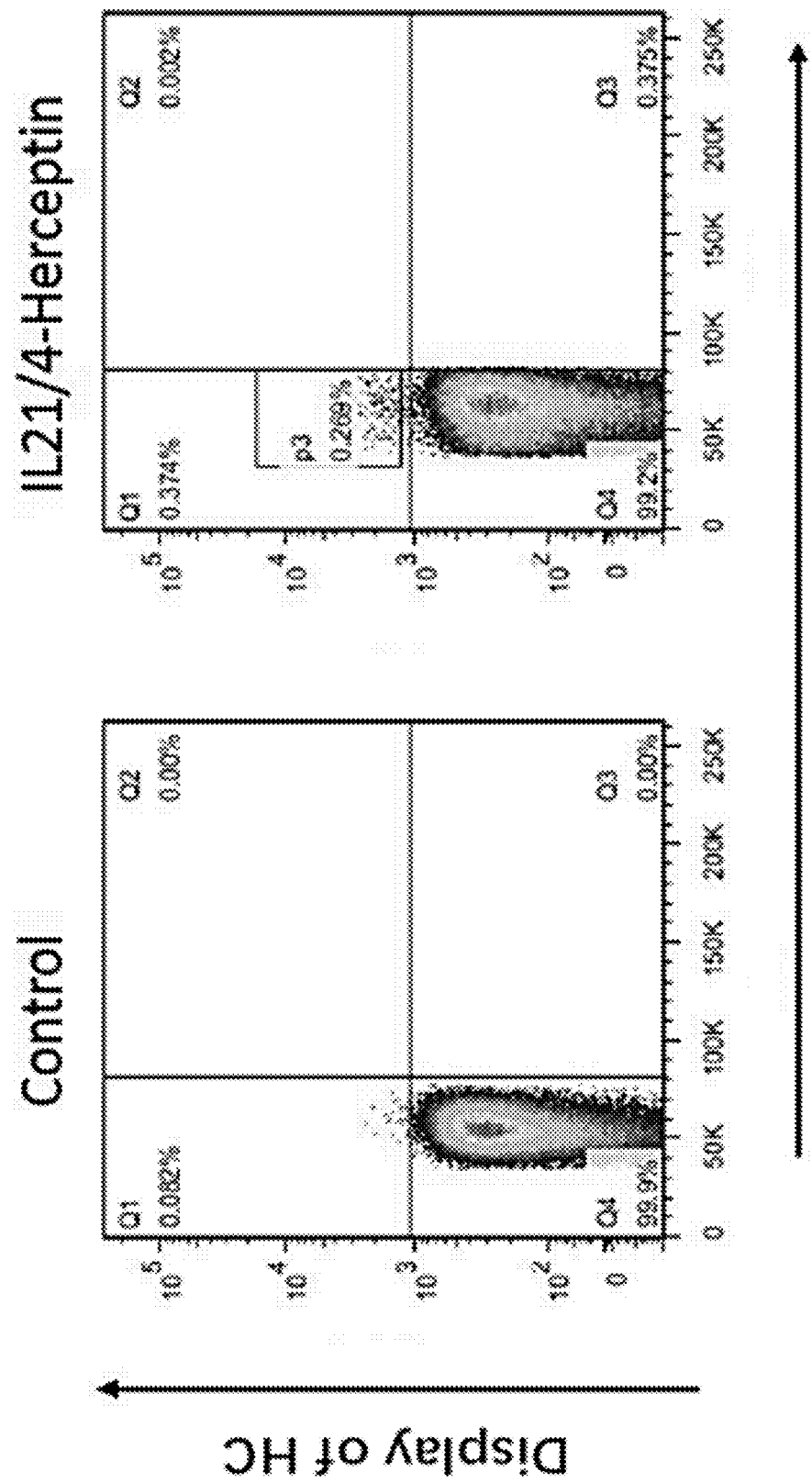
FIG. 3 shows the display rate of IL21/4-Herceptin after FRT-IL21/4-Herceptin plasmid being substituted into a CHO working cell; The left panel shows the negative control group of CHO working cell, and the right panel shows the experimental group after transfection. The ordinate presents the display rate of Herceptin HC after binding with the constant region of Herceptin heavy chain. The p3 region shows the display rate of IL21/4-Herceptin after successful substitution, which was about 0.269%.

After transfection, the cells were collected on time, and then labeled with Mouse Anti-human IgG-APC antibody. The display rate after IL21/4-Herceptin substitution was detected by flow cytometry. The results (FIG. 3) showed a display rate of 0.269%, suggesting that the probability of substitution recombination after transfection was very low. Therefore, the cells with successful substitution and positive test results were required to be detected again after enrichment. To avoid a false positive signal, the cells with a strong positive signal in p3 area of the upper left quadrant of the above figure were sorted by flow FACS Arial", then were cultured and expanded.

Figure 4:
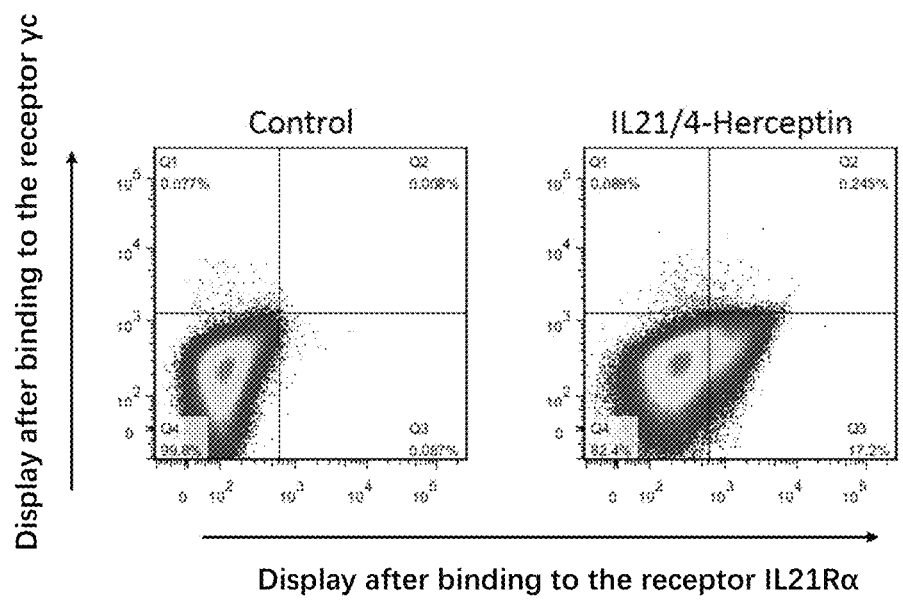
FIG. 4 shows the display rate of IL21/4-Herceptin after FRT-IL21/4-Herceptin plasmid being substituted into a CHO working cell, which was sorted and enriched; The left panel shows the negative control group of CHO working cell, and the right panel shows the experimental group after transfection. The abscissa presents the display rate after binding to the extracellular domain of IL21 receptor IL21Rα, and the ordinate presents the display rate after binding to the extracellular domain of IL21 receptor γc. The experimental group showed a display rate of 17.2% after binding to the extracellular domain of IL21Rα, and a display rate of less than 0.3% after binding to the extracellular domain of γc.

After enrichment, detection was conducted again. This time, we labeled pre-expressed and purified IL21Rα extracellular domain-linker-GFP-his fusion protein, γc extracellular domain-linker-mRFP-his fusion protein and Mouse Anti-human IgG-APC antibody, to simultaneously detect the integrity of IL21/4 and Herceptin domains in IL21/4-Herceptin fusion protein. The results were shown in FIGS. 4 and 5. As shown in FIG. 4, the abscissa presents the display rate (17.2%) of IL21/4 in IL21/4-Herceptin fusion protein after binding to the extracellular domain of IL21 receptor IL21Rα; the ordinate presents that the display rate (<0.3%) of IL21/4 in IL21/4-Herceptin fusion protein after binding to the extracellular domain of IL21 receptor γc. As reported, the affinity of IL21 binding to receptor γc was much lower than that to receptor IL21Rα, which was also confirmed for several times in present experiment.

Figure 5:
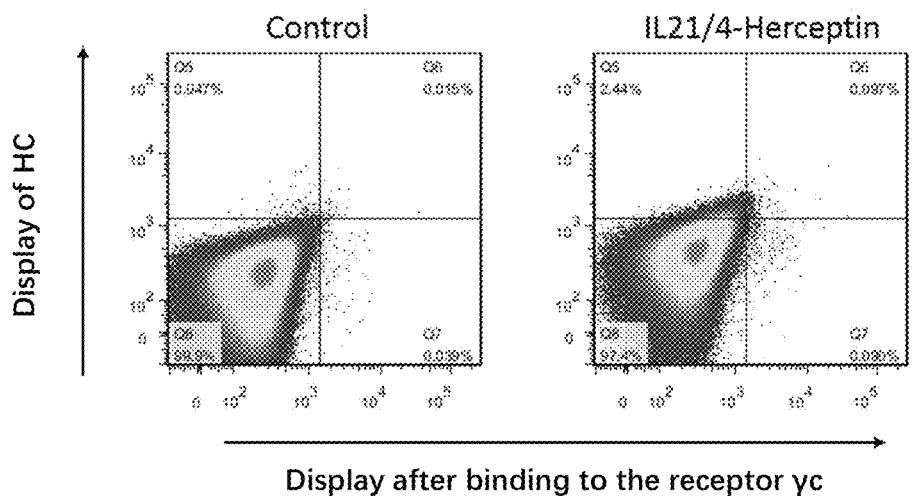
FIG. 5 shows the display rate after IL21/4-Herceptin cell binding to Mouse Anti-human IgG-APC antibody. The left panel shows the negative control group of CHO working cell, the right panel shows the experimental group after transfection. The abscissa presents the display rate after binding to the extracellular domain of IL21 receptor γc; the ordinate presents the display rate of Herceptin HC after binding to the constant region of Herceptin heavy chain. The results showed that the display rate of Herceptin after binding to the fusion protein was 2.54%.

As shown in FIG. 5, the abscissa presents that the display rate of IL21/4 in IL21/4-Herceptin fusion protein was less than 0.3% after binding to the extracellular domain of IL21 receptor γc, and the ordinate presents that the display rate of constant region of Herceptin heavy chain in fusion protein was 2.54% after binding to the labeled antibody, Mouse Anti-human IgG-APC antibody, higher than the display rate (0.26%) before enrichment. Combined with the labeling results of IL21Rα extracellular domain-linker-GFP fusion protein, it suggested that the affinity of Herceptin heavy chain constant region to the labeled antibody, Mouse Anti-human IgG-APC antibody, was lower than that to IL21Rα extracellular domain-linker-GFP.

The above-mentioned CHO cell that stably displayed IL21/4-Herceptin fusion protein was sorted by flow FACS AriaIII and named as an s0 cell.

The steps for constructing the plasmid that could stably display chimeric IL21/4 on the surface of a CHO cell in the molecular biology experimental process were as follows:
1. Constructing the pFRT-Herceptin LC-IRES-IL21/4-linker-Herceptin HC-TM-Loxp plasmid and stably displaying the mutant IL21/4 on the surface of a CHO cell:
    (1) Primers were designed with IL21 as template, and the IL21/4 fragment was obtained by overlap PCR.
    (2) The IL21/4 fragment was linked to the N-terminal of the Herceptin heavy chain HC via a linker by overlap PCR, and then the sp-IL21/4-linker-HerceptinHC fragment was substituted into the heavy chain part of the antibody displaying plasmid pFRT constructed in our laboratory, so as to construct the pFRT-Herceptin LC-IRES-IL21/4-linker-Herceptin HC-TM-Loxp plasmid. The plasmid could stably display the mutant IL21/4 on the surface of a CHO cell.
2. Constructing a plasmid that could secrete and express IL21Rα-linker-GFP fusion protein, and secreting and expressing the extracellular domain of IL21 receptor α to examine the functional activity of IL21:
    (1) Through querying database, the extracellular domain of IL21 receptor IL21Rα chain was synthesized, and then primers were designed to amplify the GFP fragment by PCR with GFP as a template.
    (2) The extracellular domain of IL21Rα chain was linked to the N-terminal of GFP via a linker by overlap PCR, and then the extracellular domain-linker-GFP fragment of sp-IL21 Rα chain was linked into pCEP4, so as to construct a plasmid that could secrete and express IL21Rα-linker-GFP fusion protein.
3. Constructing a plasmid that could secrete and express γc-linker-mRFP fusion protein, and secreting and expressing the extracellular domain of IL21 receptor γc to examine the functional activity of IL21:
    Through querying database, the extracellular domain of IL21 receptor γc chain was synthesized, and then, again, primers were designed to amplify the mRFP fragment by PCR with mRFP as a template. Again, the extracellular domain of γc chain was linked to the N-terminal of mRFP via a linker by overlap PCR, and then, again, the extracellular domain-linker-mRFP fragment of sp-γc chain was linked into pCEP4, so as to construct a plasmid that could secrete and express γc-linker-GFP fusion protein.
4. Constructing a plasmid that could secrete and express IL21 mutant and fusion protein:
    (2) Construction of plasmids that could stably display various mutants of IL21: In order to stably display another mutant of IL21 on the surface of a CHO cell, we used point mutation PCR to construct a plasmid: using pFRT-Herceptin LC-IRES-IL21/4-linker-Herceptin HC-TM-Loxp plasmid as a template to design primers, so as to construct plasmids that could stably display different mutants of IL21.
    (3) Construction of plasmids that could secrete and express IL21 mutant protein: Using plasmids that could display various IL21 mutants as templates to design primers, amplifying IL21 mutant fragments by PCR, and then linking them into pCEP4, so as to construct plasmids that could secrete and express IL21 mutant protein.

Example 2. Study on the Stability of IL21/4 by Introducing a Disulfide Bond at Different Sites Through Protein Design 1. Through analyzing and designing protein structure, different sites on IL21/4 protein were selected for mutation, and a disulfide bond was introduced to obtain the following groups of mutants. The disulfide bond was introduced as follows:

(1) ILE at position 16 and SER at position 70 were both mutated to CYS, 16-70 disulfide bond was introduced; named as 16cIL21/4;
(2) ILE at position 17 and SER at position 106 were both mutated to CYS, 17-106 disulfide bond was introduced; named as 17cIL21/4;
(2) ILE at position 16, SER at position 70, VAL at position 17 and LYS at position 106 were all mutated to CYS, two groups of disulfide bonds were introduced at the same time; named as 4cIL21/4.

2. Obtaining a CHO cell that could stably display each of IL21/4 mutants.

In order to obtain a CHO cell line that could stably display each of IL21/4 mutants, with FRT-IL21/4-Herceptin as a template, recombinant substitution plasmids of each of IL21/4 mutants were firstly obtained by point mutation technique, named as 16cIL21/4-Herceptin, 17cIL21/4-Herceptin and 4cIL21/4-Herceptin. A CHO working cell was co-transfected with above plasmids and pre-constructed pci-2A plasmid again, and enriched after successful recombination and substitution. The display rate was detected by binding to the labeled antibody, Mouse Anti-human IgG-APC antibody.

Figure 6:
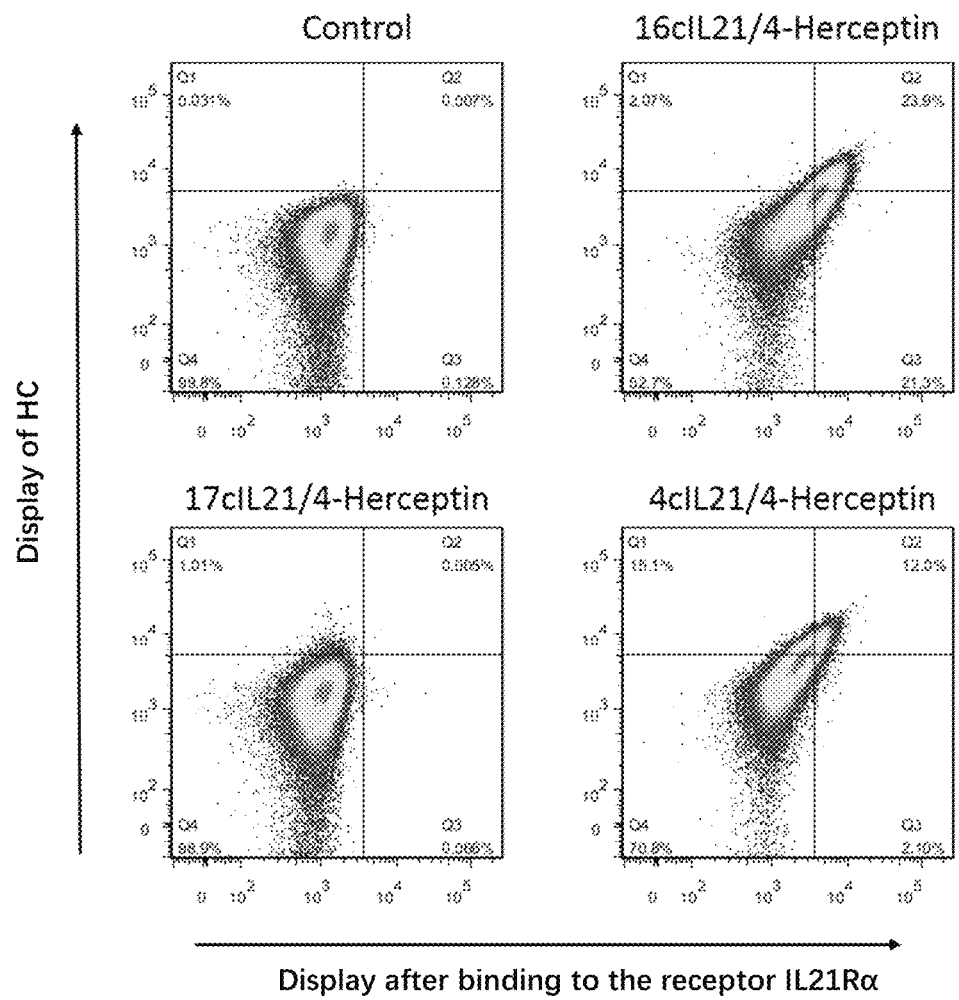
FIG. 6 shows the display rate of IL21/4-Herceptin detected after mutating the disulfide bond. The shown display rate results were from CHO cells after enrichment, which displayed 16c IL21/4-Herceptin, 17c IL21/4-Herceptin and 4c IL21/4-Herceptin protein. The abscissa presents the display rate after binding to the extracellular domain of IL21 receptor IL21Rα; the ordinate presents the display rate after the constant region of Herceptin heavy chain binding to the labeled antibody, Mouse Anti-human IgG-APC antibody. It shows that the display rate of 16cIL21/4-Herceptin and 4cIL21/4-Herceptin group after binding to the constant region of Herceptin heavy chain was significantly higher than that before enrichment; while the display rate of 17cIL21/4-Herceptin group after binding to the constant region of Herceptin heavy chain is only 1% after enrichment. It shows that the display rate of 16cIL21/4-Herceptin and 4cIL21/4-Herceptin groups after binding to the extracellular domain of receptor IL21Rα was significantly higher than that before enrichment; while there was no obvious binding between the 17cIL21/4-Herceptin group and the extracellular domain of receptor IL21Rα, as similar to that of the control group.

As shown in FIG. 6, the abscissa represents the display rate of various mutant IL21/4-Herceptin fusion proteins after binding to the extracellular domain of IL21 receptor IL21Rα. The ordinate represents the display rate of the constant region of Herceptin heavy chain in fusion protein after binding to the labeled antibody, Mouse Anti-human IgG-APC antibody. As shown, the display rate of 16cIL21/4-Herceptin and 4cIL21/4-Herceptin were significantly higher than those before enrichment, and bound to the extracellular domain of receptor IL21Rα very well. However, the ordinate of the control group, 17cIL21/4-Herceptin, represents a display rate of only 1% after binding to the labeled antibody, Mouse Anti-human IgG-APC antibody. There was no obvious binding to the extracellular domain of the receptor IL21Rα. This indicated that the mutant of the control group, 17cIL21/4-Herceptin, was not displayed.

We had obtained a CHO working cell that could stably display two kinds of IL21/4 mutants on the surface of cell membrane, and then we would do a preliminary stability test of these two IL21/4 mutants.

Example 3. Preliminary Stability Test of Each of the IL21/4 Mutants

To test the stability of each of the IL21/4 mutants, the CHO working cells displaying IL21/4-Herceptin and the CHO working cells displaying mutants 16cIL21/4-Herceptin and 4cIL21/4-Herceptin were used as an experimental group. Each group was heated at various temperature gradients of 4° C.-50° C., and then bound and labeled with IL21 receptor IL21Rα extracellular domain-linker-GFP-his. The display rate of each group was detected by flow cytometry after binding to the receptor at various temperature gradients. As temperature changing, a protein with poor thermal stability would be denatured first, the normal conformation would be destroyed, and the ability of receptor binding would lose. Through this way, the thermal stability of each mutant could be examined.

The particular experimental processes were as follows:
(1) CHO cells that stably displaying IL21 mutant on the surface of cell membrane were digested with 0.02% EDTA-PBS, eluted with a medium containing serum, and centrifuged at 830 g for 3 min. The supernatant was discarded and the cells were collected.
(2) The cells were re-suspended in 1 ml serum-free Opti-MEM medium precooled at 4° C., centrifuged at 830 g for 3 min. The supernatant was discarded and the cells were collected. The cells were then re-suspended in serum-free Opti-MEM medium precooled at 4° C. again, to about $5 \times 10^6$ cells/50 μl.
(3) The cell suspension was added into a PCR tube and heated with temperature gradient set by a PCR instrument. The PCR tube was heated at the preset temperature for 0.5 h. The PCR tube was kept at 4° C. for 15 min, before being removed.
(4) The extracellular domain of IL21 receptor was added in certain proportion, and thoroughly mixed with fluorescent protein fusion protein. The mixture was kept on a shaker at 4° C. for 1 h away from light.
(5) The mixture was centrifuged at 830 g for 3 min, the supernatant was discarded. New Opti-MEM precooled at 4° C. was added to wash the precipitate twice through centrifuging and discarding supernatant. Then, the precipitate was re-suspended with 200 μl OPTI-MEM precooled at 4° C. The labeled cells were detected or sorted by FACSAriaIII(BD) or FACSCalibur.

The results showed that,
(1) At 4° C., except the negative control group, all groups bound to the extracellular domain of IL21 receptor IL21Rα. The display rate of mutant 16cIL21/4-Herceptin was 20%, which was the highest binding rate.
(2) After heating at 49° C., the binding of IL21/4-Herceptin group and 4cIL21/4-Herceptin group to the extracellular domain of IL21 receptor was substantially lost, while the binding of mutant 16cIL21/4-Herceptin group to the extracellular domain of IL21 receptor were still detectable. This could preliminarily suggest that the mutant 16cIL21/4 had an improved thermal stability.

Example 4. Construction of Wild-Type IL21 Mutant and Preliminary Stability Test

1. Detection of Thermal Stability of Mutant by Flow Cytometry.

In order to study the effect of introducing a disulfide bond at the same positions (positions 16 and 70) on stability in wild-type IL21 molecule, we constructed two other structures:

IL21-Herceptin: The Fusion Protein of Wild-Type IL21 and Herceptin;

16cIL21-Herceptin: the fusion protein constructed by Herceptin and IL21, wherein, at the same positions, ILE at position 16—SER at position 70, were mutated to CYS and introduced a disulfide bond;

They were also displayed on the surface of CHO working cell membrane by transfection and substitution recombination, and then were compared with 16cIL21/4-Herceptin and IL21/4-Herceptin. They were heated at different temperature gradients from 4° C.-55° C., and labeled by binding to IL21 receptor IL21Rα extracellular domain-linker-GFP-his and the labeled antibody, Mouse Anti-human IgG-APC antibody. The display rate of each group was detected by flow cytometry after binding to the receptor at various temperature gradients.

The results showed that 16cIL21/4-Herceptin and 16cIL21-Herceptin with introduced 16-70 disulfide bond still had a partial display rate after binding to the receptor after being heated to 48° C., indicating that their stability was higher than that of IL21/4-Herceptin and IL21-Herceptin. These four proteins were a fusion protein. The detection by flow cytometry was only a preliminary sorting. It was necessary to express each of IL21 and mutant proteins, and further identify the thermal stability after purification.

2. Expression of IL21 and its Mutant Proteins and Detection of Disulfide Bond Structure.

Figure 7:
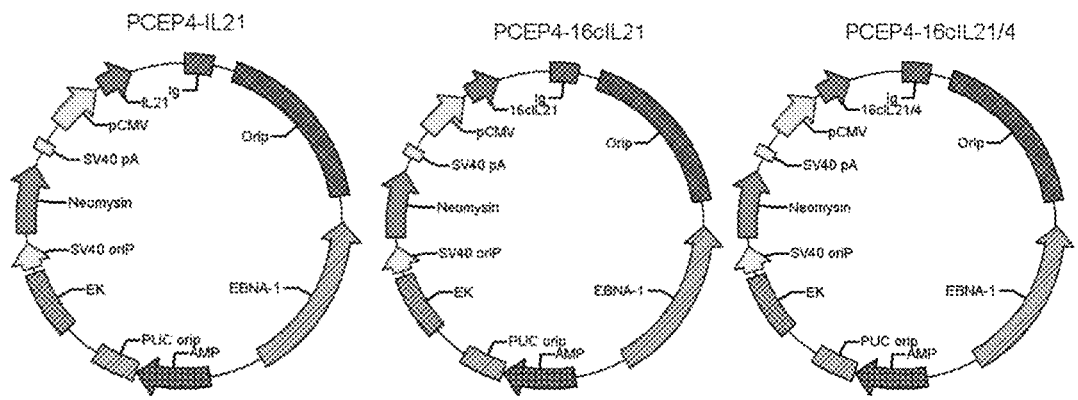
FIG. 7 shows the construction of expression plasmids of various mutant proteins IL21, 16cIL21 and 16c IL21/4 (structure graph). The gene encoding each mutant protein was inserted into a PCEP4 vector to construct an expression plasmid, in which a His tag was added.

In order to obtain IL21 and its mutant proteins, a plasmid was firstly constructed. IL21 and mutant coding genes were inserted into PCEP4 vector plasmids respectively, in which a His tag was added. Three plasmids expressing IL21, 16cIL21 and 16cIL21/4 mutant proteins were constructed respectively (FIG. 7).

Figure 8:
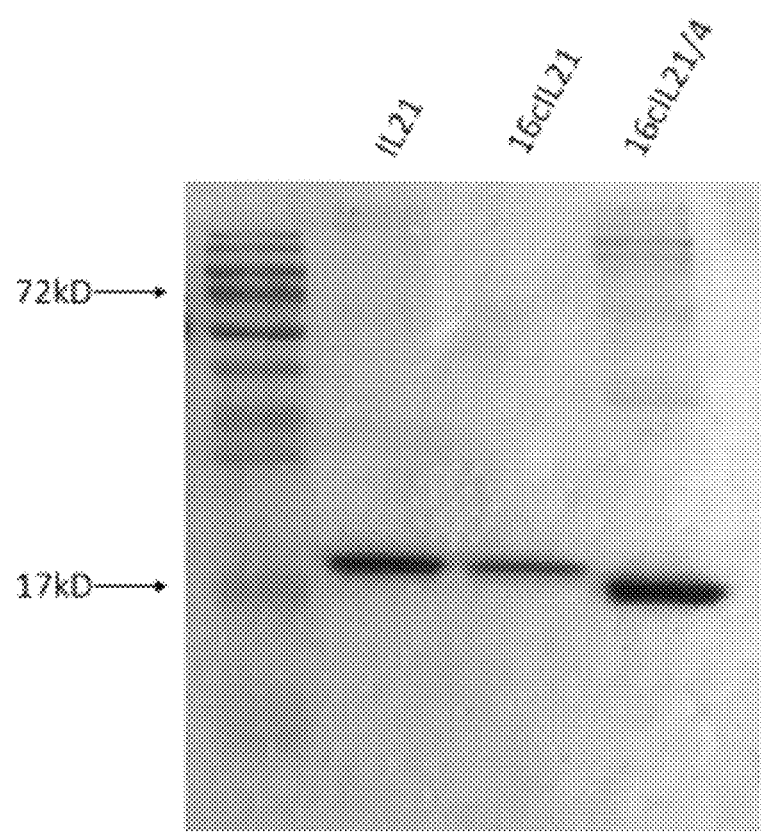
FIG. 8 shows the SDS-PAGE gel electrophoresis results of IL21 and each of the mutant proteins.

The SDS-PAGE electrophoresis were conducted for IL21, 16cIL21 and 16cIL21/4 proteins, and the results were shown in FIG. 8. From the results, the bands of IL21, 16cIL21 and 16cIL21/4 were consistent with their molecular weight in theory. From the molecular weights, these three proteins were the target proteins.

Mass spectrometry was further performed to confirm the formation of the target disulfide bond in 16cIL21/4 protein. The 16cIL21/4 protein was detected by mass spectrometry, and the disulfide bond should be prevented from being broken during electrophoresis. The sample protein was firstly hydrolyzed by protease and cut into peptide segments of various sizes. The disulfide bond in the protein would affect the result of enzymolysis. Under the condition that the disulfide bond was broken or not, the sample protein would be cut into peptide segments of different sizes and the peptide segments should have different distributions of mass-to-charge ratio. According to the consistency of the detected distribution with the theoretical distribution, it could determine if there was a disulfide bond in the sample protein.

Figure 9:
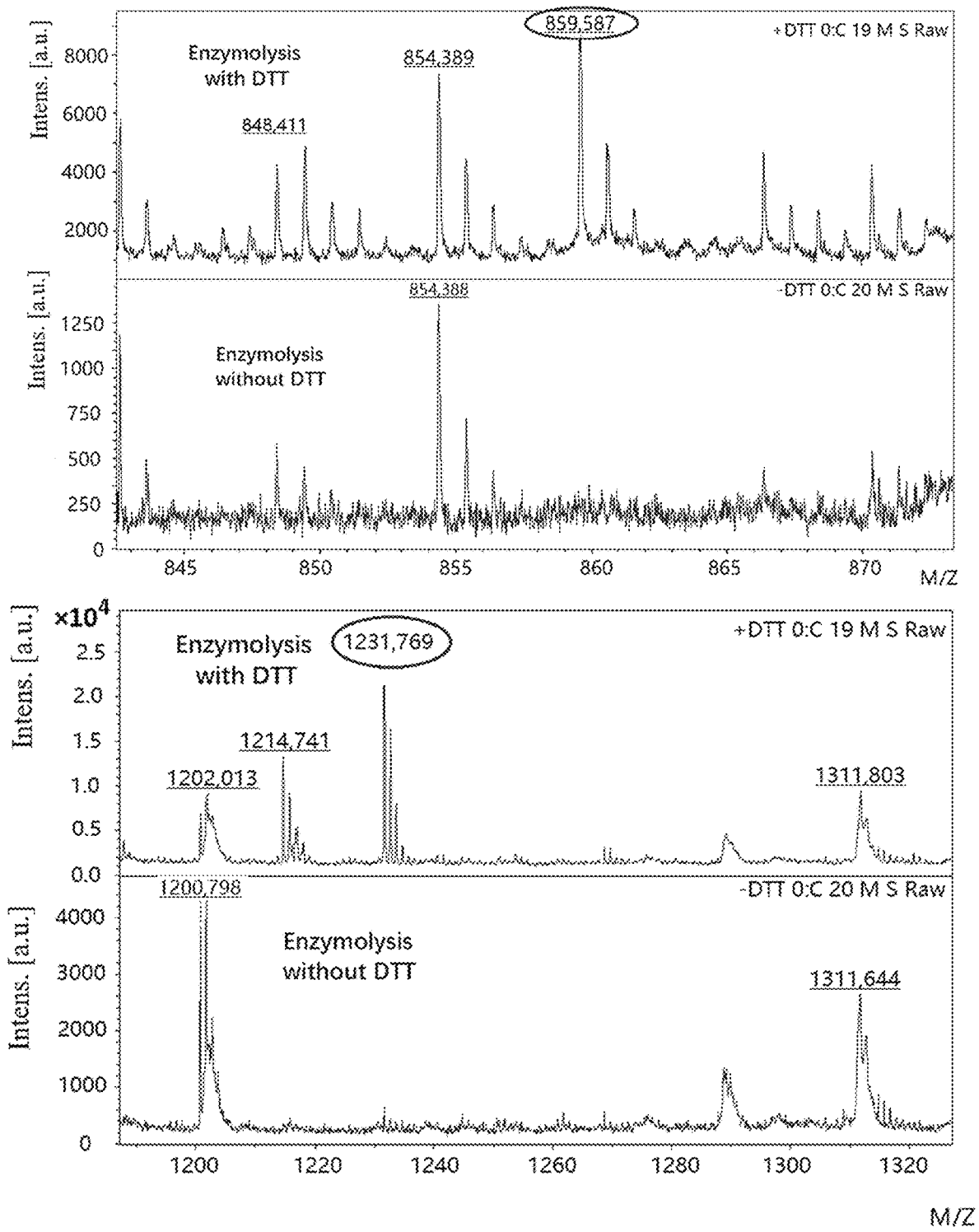
FIG. 9 shows the mass spectrogram of 16cIL21 and 16cIL21/4 mutant proteins after enzymatic hydrolysis.
Figure 9:
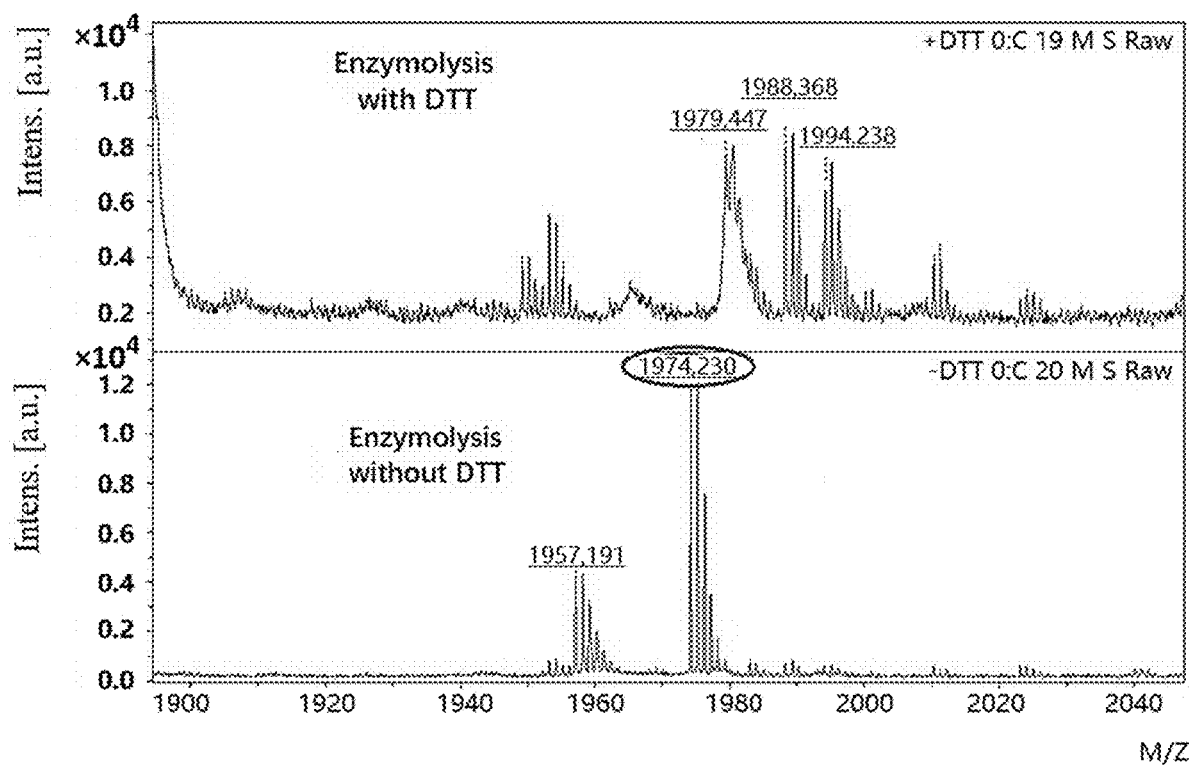

Analysis of the Disulfide Bond in the Sample 16cIL21/4:

The amino acid sequences of the two segments that would generate a disulfide bond in theory were IINVCIK and QLIDCVDQLK. When enzymolysis was carried out in a reduced state, the disulfide bond was broken and C would be alkylated (the molecular weight would increase by 57 Da). The theoretical values of mass-to-charge ratio of the two peptide segments were 859.507 and 1231.635, respectively. As shown in FIG. 9A, there were obvious signal peaks at 859.587 and 1231.769 in the reduced state (with DTT), while the two signal peaks were very low in a non-reduced state. The results suggested that the disulfide bond was broken and two peptide segments were generated in the 16cIL21/4 sample protein when adding DTT. Not adding DTT, the disulfide bond would not be broken, and there was no signal of the two peptide segments. This was consistent with the disulfide bond structure of theoretical prediction.

If enzymolysis was carried out in a non-reduced state, the disulfide bond between the two peptide segments was not broken. We could detect a peptide with a mass-to-charge ratio equal to the sum of that of the two peptide segments. The theoretical mass-to-charge ratio of the sum of the two peptide segments would be (859.587−57)+(1231.769−57)−2−1=1974.356 in a non-reduced state. In FIG. 9B, we could see an obvious peak with a mass-to-charge ratio of 1974.230 in the non-reduced state, while the signal of this peak was very poor in a reduced state. This suggested that the disulfide bond of sample protein was not broken when not adding DTT, and thus the enzymolysis product had the signal of a large peptide segment. When adding DTT, the disulfide bond would be broken and the larger peptide segment was split, and thus the signal disappeared.

The above results were also observed during the enzymolysis of 16cIL21 protein, which indicated that a disulfide bond was rightly formed between C at position 16 and C at position 70.

3. Determination of Melting Temperature (Tm) of IL21 and Each of the Mutant Proteins.

Figure 10:
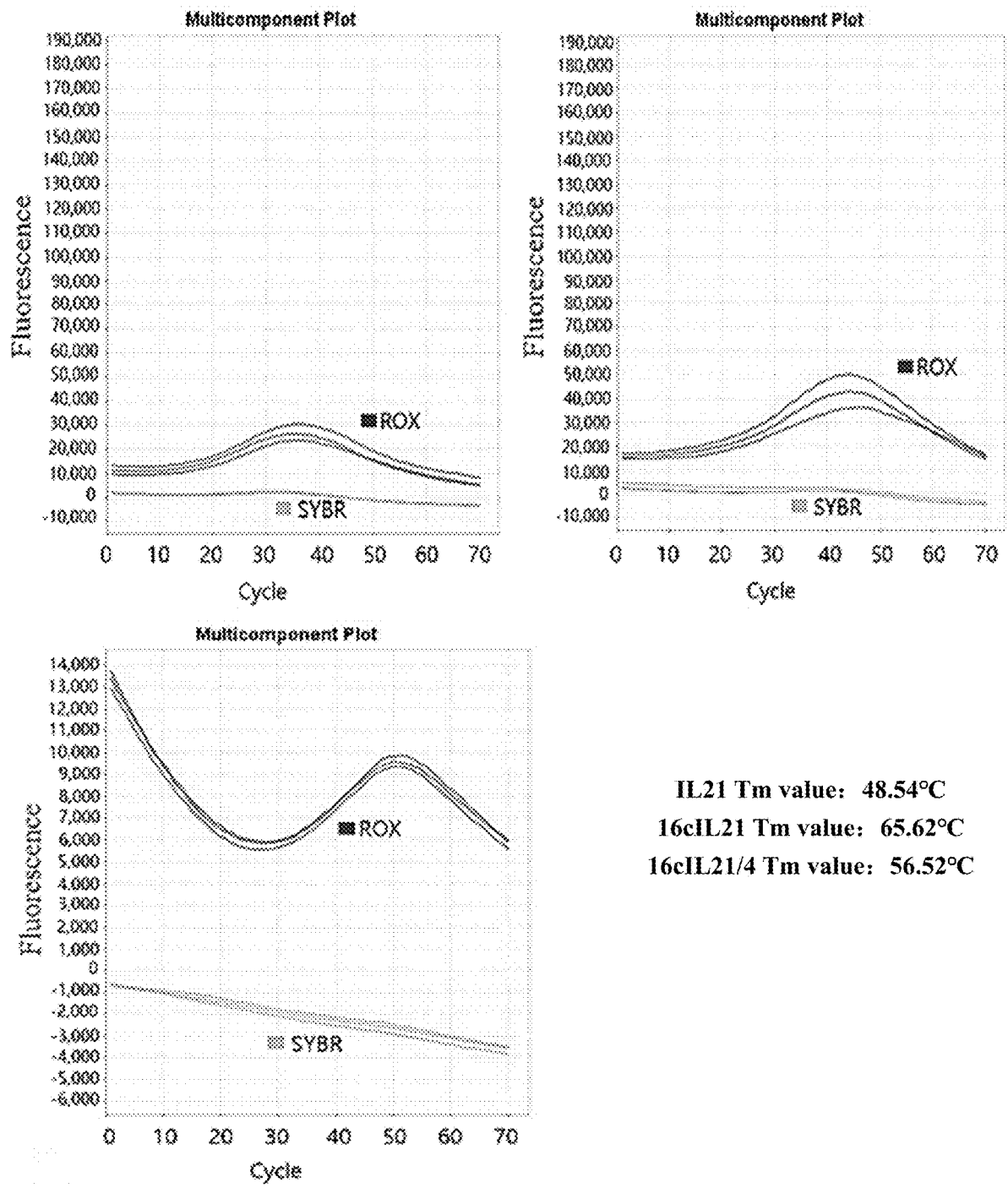
FIG. 10 shows the melting temperatures (Tm) of IL21, 16cIL21 and 16cIL21/4 to determine the thermal stability of IL21 and each of the mutant proteins.

After the formation of a disulfide bond between cys at positions 16 and position 70 in 16cIL21/4 protein was confirmed, we measured the melting temperature (Tm) of three proteins, IL21, 16cIL21 and 16cIL21/4, to determine the thermal stability of IL21 and each of the mutant proteins. The results were shown in FIG. 10:

As shown in the results, the Tm values of IL21, 16cIL21 and 16cIL21/4 were as follows: 16cIL21 (65.62° C.)>16cIL21/4 (56.52° C.)>IL21 (48.54° C.).

The results suggested that the thermal stability of the two mutants 16cIL21 and 16cIL21/4 proteins with a disulfide bond was significantly higher than that of the wild-type IL21 protein. It could be considered that the introduction of disulfide bond would be the reason for improving the thermal stability.

Example 5. Determination of Biological Activities of Various IL21 Mutants

1. The Ability of Stimulating the Proliferation of a KOB Cell.

We detected whether the biological activities of three proteins, IL21, 16cIL21 and 16cIL21/4, were remained while the thermal stability was improved. KOB cells express IL21 receptor and can be stimulated by IL21 to proliferate. The biological activity of various IL21 mutants could be determined by the ability of stimulating the proliferation of KOB cell. The particular processes were as follows:
  (1) Preparation of KOB cell: The KOB cells were cultured in RPMI1640 medium containing 10% calf serum (Hyclone) and 100 U/mL double antibody, in 5% $CO_2$ incubator at 37° C.
  (2) Preparation of IL21 and the mutant proteins: The expression plasmids of IL21 and the mutant proteins (with His tag) were constructed and transfected into 293F cells. The steps of culture, expression and purification by nickel column were conducted conventionally. The protein concentration was determined by BCA assay.
  (3) Determination of biological activity: KOB cells were seeded in a 96-well plate with $2 \times 10^4$ cells/well, and 200 μl culture medium and IL21 or a mutant protein was added into each well. The gradient concentration of IL21 or mutant protein was set to 0.1 ng/ml, 1 ng/ml and 10 ng/ml. The cells were cultured in 5% $CO_2$ incubator at 37° C., and counted after 96 hours.

The results were shown in FIG. 11:

According to the results of non-repeated Two-Way Analysis of Variance, the p value between control group and each protein group was less than 0.05 (p<0.05), indicating that there was a significant difference between groups. The p value among the three protein groups is above 0.05 (P>0.05), indicating that there was no significant difference among the three protein groups. The p value among the groups with different concentrations of the three proteins was above 0.05 (P>0.05), indicating that there was no significant difference among the groups with different concentrations of the three proteins.

From this result, all the three proteins had an effect of stimulating the proliferation of KOB cell and had no significant difference in biological activity. When the gradient concentrations of added protein were 0.04 μg/ml, 0.2 g/ml and 1 g/ml, there was no significant difference between the groups with different concentrations of protein.

Therefore, the two mutant proteins, 16cIL21 and 16cIL21/4, had improved thermal stability and remained the biological activity.

2. Test Results of Plasma Half-Life of the Fusion Protein of Herceptin and IL21 or Each of the Mutants in Mouse To determine whether the improved stability of IL21 could increase the plasma half-life in animal, we selected IL21-Herceptin fusion protein, mutated 16cIL21-Herceptin fusion protein and 16cIL21/4-Herceptin fusion protein for comparison test to detect their plasma half-life in mouse. The Herceptin group was used as a control group. The results were shown in Table 4:

TABLE 4

Half-life of different types of IL21/fusion proteins.

|  | IL21-Herceptin | 16cIL21-Herceptin | 16cIL21/4-Herceptin | Herceptin |
|---|---|---|---|---|
| Half-life of IL21chimeric block | 44.14 h | 161.18 h | 198.02 h | — |
| Half-life of Herceptin chimeric block | 364.78 h | 187.32 h | 385.05 h | 462.06 h |

As shown in the results, the highly stable IL21 mutant contained in 16cIL21-Herceptin and 16cI21/4-Herceptin fusion protein had significantly increased plasma half-life compared with wild-type IL21 in mouse. The 16cIL21/4-Herceptin fusion protein had the longest plasma half-life. This suggested that the improved stability of IL21 was an important reason for increasing plasma half-life.

3. Determination of T Cells Proliferation Stimulated by IL21 Fusion Protein.

The functional activity of 16cIL21/4-Herceptin fusion protein was detected using BT474 breast cancer-bearing mouse model. $1.5 \times 10^7$ human BT474 breast cancer cells were inoculated on the right abdomen or back of a mouse. The fusion protein was administered after 35 days. The proliferation of CD8+T cells stimulated by 16cIL21/4-Herceptin fusion protein and Herceptin in the mouse was detected. The results were shown in FIG. 12. In the 16cI21/4-herceptin fusion protein group, the proportion of CD8+T cells in peripheral blood showed an obvious increase about 53 days after tumor inoculation. Meanwhile, T cells in Herceptin group had a tendency of slowly decreasing.

4. Tumor Inhibitory Effect of IL21 Fusion Protein.

The tumor inhibitory effect of 16cIL21/4-Herceptin fusion protein was detected using BT474 breast cancer-bearing mouse model. Each mouse was inoculated with $1 \times 10^7$ BT474 cells (human breast cancer cells). The mice were injected intraperitoneally with PBS (Control), Herceptin (Herceptin alone), 16cIL21/4-Herceptin fusion protein (IL-21$_{mutant}$-Herceptin) and the mixed solution of 16cIL21/4 and Herceptin (IL-21$_{mutant}$+Herceptin) once every four days. The dosage of each injection was 500 μg. The results were shown in FIG. 13. Compared with the control group, Herceptin group and mixed solution group, 16cIL21/4-Herceptin fusion protein group significantly reduced tumor volume.

In the end, it should be noted that the above examples are only used to help those skilled in the art understand the essence of the present invention, and should not be used to limit the protection scope of the present invention.

What is claimed is:

1. An interleukin-21 (IL21) mutant that is derived from a wild-type IL-21 comprising the amino acid sequence of SEQ ID NO:1, and that comprises the amino acid substitutions I16C and S70C.

2. A medicine or pharmaceutical composition comprising the IL21 mutant of claim 1 as an active ingredient.

3. A polynucleotide encoding the IL21 mutant of claim 1.

4. An interleukin-21 and interleukin-4 chimeric protein (IL21/4) mutant that is derived from a chimeric protein (IL21/4) comprising the amino acid sequence of SEQ ID NO:2, and that comprises the amino acid substitutions I16C and S70C.

5. A medicine or pharmaceutical composition comprising the IL21/4 mutant of claim 4 as an active ingredient.

6. A polynucleotide encoding the IL21/4 mutant of claim 4.

* * * * *

SEQUENCE LISTING

```
<160> NUMBER OF SEQ ID NOS: 6

<210> SEQ ID NO 1
<211> LENGTH: 133
<212> TYPE: PRT
<213> ORGANISM: Artificial Sequence
<220> FEATURE:
<223> OTHER INFORMATION: Synthetic construct

<400> SEQUENCE: 1

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
```

Gly Ser Glu Asp Ser
    130

<210> SEQ ID NO 2
<211> LENGTH: 127
<212> TYPE: PRT
<213> ORGANISM: Artificial Sequence
<220> FEATURE:
<223> OTHER INFORMATION: Synthetic construct

<400> SEQUENCE: 2

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Asn Leu Trp Gly
65                  70                  75                  80

Leu Ala Gly Leu Asn Ser Cys Pro Ser Cys Asp Ser Tyr Glu Lys Lys
                85                  90                  95

Pro Pro Lys Glu Phe Leu Glu Arg Phe Lys Ser Leu Leu Gln Lys Met
            100                 105                 110

Ile His Gln His Leu Ser Ser Arg Thr His Gly Ser Glu Asp Ser
        115                 120                 125

<210> SEQ ID NO 3
<211> LENGTH: 133
<212> TYPE: PRT
<213> ORGANISM: Artificial Sequence
<220> FEATURE:
<223> OTHER INFORMATION: Synthetic construct

<400> SEQUENCE: 3

Gln Gly Gln Asp Arg His Met Ile Arg Met Arg Gln Leu Ile Asp Cys
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Cys Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser
    130

<210> SEQ ID NO 4
<211> LENGTH: 127

<212> TYPE: PRT
<213> ORGANISM: Artificial Sequence
<220> FEATURE:
<223> OTHER INFORMATION: Synthetic construct

<400> SEQUENCE: 4

```
Gln Gly Gln Asp Arg His Met Ile Arg Met Arg Gln Leu Ile Asp Cys
1               5                   10                  15
Val Asp Gln Leu Lys Asn Tyr Val Asn Asp Leu Val Pro Glu Phe Leu
            20                  25                  30
Pro Ala Pro Glu Asp Val Glu Thr Asn Cys Glu Trp Ser Ala Phe Ser
        35                  40                  45
Cys Phe Gln Lys Ala Gln Leu Lys Ser Ala Asn Thr Gly Asn Asn Glu
    50                  55                  60
Arg Ile Ile Asn Val Cys Ile Lys Lys Leu Lys Arg Asn Leu Trp Gly
65                  70                  75                  80
Leu Ala Gly Leu Asn Ser Cys Pro Ser Cys Asp Ser Tyr Glu Lys Lys
                85                  90                  95
Pro Pro Lys Glu Phe Leu Glu Arg Phe Lys Ser Leu Leu Gln Lys Met
            100                 105                 110
Ile His Gln His Leu Ser Ser Arg Thr His Gly Ser Glu Asp Ser
        115                 120                 125
```

<210> SEQ ID NO 5
<211> LENGTH: 133
<212> TYPE: PRT
<213> ORGANISM: Artificial Sequence
<220> FEATURE:
<223> OTHER INFORMATION: Synthetic construct

<400> SEQUENCE: 5

```
Gln Gly Gln Asp Arg His Met Ile Arg Met Arg Gln Leu Ile Asp Cys
1               5                   10                  15
Cys Asp Gln Leu Lys Asn Tyr Val Asn Asp Leu Val Pro Glu Phe Leu
            20                  25                  30
Pro Ala Pro Glu Asp Val Glu Thr Asn Cys Glu Trp Ser Ala Phe Ser
        35                  40                  45
Cys Phe Gln Lys Ala Gln Leu Lys Ser Ala Asn Thr Gly Asn Asn Glu
    50                  55                  60
Arg Ile Ile Asn Val Cys Ile Lys Lys Leu Lys Arg Lys Pro Pro Ser
65                  70                  75                  80
Thr Asn Ala Gly Arg Arg Gln Lys His Arg Leu Thr Cys Pro Ser Cys
                85                  90                  95
Asp Ser Tyr Glu Lys Lys Pro Pro Lys Glu Phe Leu Glu Arg Phe Cys
            100                 105                 110
Ser Leu Leu Gln Lys Met Ile His Gln His Leu Ser Ser Arg Thr His
        115                 120                 125
Gly Ser Glu Asp Ser
        130
```

<210> SEQ ID NO 6
<211> LENGTH: 127
<212> TYPE: PRT
<213> ORGANISM: Artificial sequence
<220> FEATURE:
<223> OTHER INFORMATION: Synthetic construct

<400> SEQUENCE: 6

```
Gln Gly Gln Asp Arg His Met Ile Arg Met Arg Gln Leu Ile Asp Cys
```

```
1               5                   10                  15

Cys Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
            35                  40                  45

Cys Phe Gln Lys Ala Gln Leu Lys Ser Ala Asn Thr Gly Asn Asn Glu
        50                  55                  60

Arg Ile Ile Asn Val Cys Ile Lys Lys Leu Lys Arg Asn Leu Trp Gly
65                  70                  75                  80

Leu Ala Gly Leu Asn Ser Cys Pro Ser Cys Asp Ser Tyr Glu Lys Lys
                85                  90                  95

Pro Pro Lys Glu Phe Leu Glu Arg Phe Cys Ser Leu Leu Gln Lys Met
            100                 105                 110

Ile His Gln His Leu Ser Ser Arg Thr His Gly Ser Glu Asp Ser
            115                 120                 125
```